(12) United States Patent
Joveniaux

(10) Patent No.: US 12,239,154 B2
(45) Date of Patent: Mar. 4, 2025

(54) DEVICE FOR DECONTAMINATING A TURBID LIQUID

(71) Applicant: BIOSAFELIGHT, Orléans (FR)

(72) Inventor: Christophe Joveniaux, Chanteau (FR)

(73) Assignee: BIOSAFELIGHT, Orléans (FR)

( * ) Notice: Subject to any disclaimer, the term of this patent is extended or adjusted under 35 U.S.C. 154(b) by 1108 days.

(21) Appl. No.: 17/049,738

(22) PCT Filed: Apr. 23, 2019

(86) PCT No.: PCT/EP2019/060377
§ 371 (c)(1),
(2) Date: Oct. 22, 2020

(87) PCT Pub. No.: WO2019/206915
PCT Pub. Date: Oct. 31, 2019

(65) Prior Publication Data
US 2021/0244051 A1     Aug. 12, 2021

(30) Foreign Application Priority Data

Apr. 24, 2018   (EP) ..................................... 18169017

(51) Int. Cl.
*A23L 3/28*     (2006.01)
*A61L 2/10*     (2006.01)

(52) U.S. Cl.
CPC ...................................... *A23L 3/28* (2013.01)

(58) Field of Classification Search
CPC ............... A23L 3/28; C02F 2201/3223; C02F 2303/04; C02F 1/325; A61L 2/26; A61L 2/10
See application file for complete search history.

(56) References Cited

U.S. PATENT DOCUMENTS 5,780,860 A  *  7/1998  Gadgil ...................... A61L 2/10
                                                            250/435
6,916,452 B1 *  7/2005  Rix .......................... A61L 2/10
                                                            210/748.11

FOREIGN PATENT DOCUMENTS

DE         909 292 C       4/1954
DE         40 25 078 A1    2/1992
(Continued)

OTHER PUBLICATIONS

International Search Report for corresponding International Application No. PCT/EP2019/060377 mailed May 24, 2019.
(Continued)

*Primary Examiner* — Kevin Joyner
(74) *Attorney, Agent, or Firm* — Chrisman Gallo Tochtrop LLC

(57) ABSTRACT

The device for decontaminating a turbid liquid, in particular of the food type, includes a sheath extending longitudinally along an axis X, including an outer wall and an inner wall substantially coaxial with each other and delimiting an annular circulation space of the liquid to be decontaminated, a source of ultraviolet rays positioned in a central space delimited by the inner wall of the sheath, coaxially with the annular circulation space, the outer wall comprising a cylindrical surface facing the annular circulation space having a profile along a generatrix of the cylindrical surface comprising a succession of concave and convex shapes alternately.

12 Claims, 2 Drawing Sheets

(56) References Cited

FOREIGN PATENT DOCUMENTS

EP  1255444 A2  11/2002
WO  01/37675 A2  5/2001

OTHER PUBLICATIONS

Written Opinion for corresponding International Application No. PCT/EP2019/060377 dated May 24, 2019.

\* cited by examiner

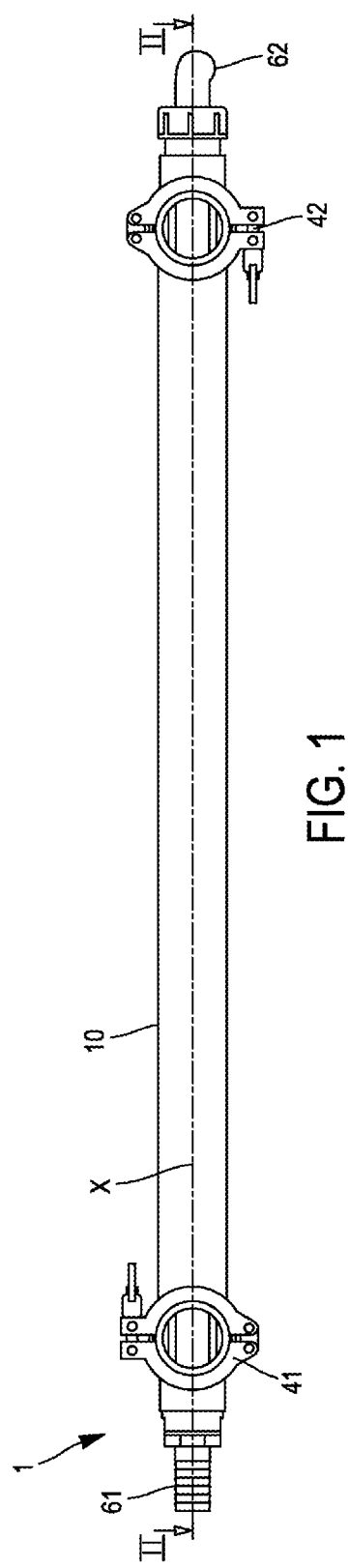
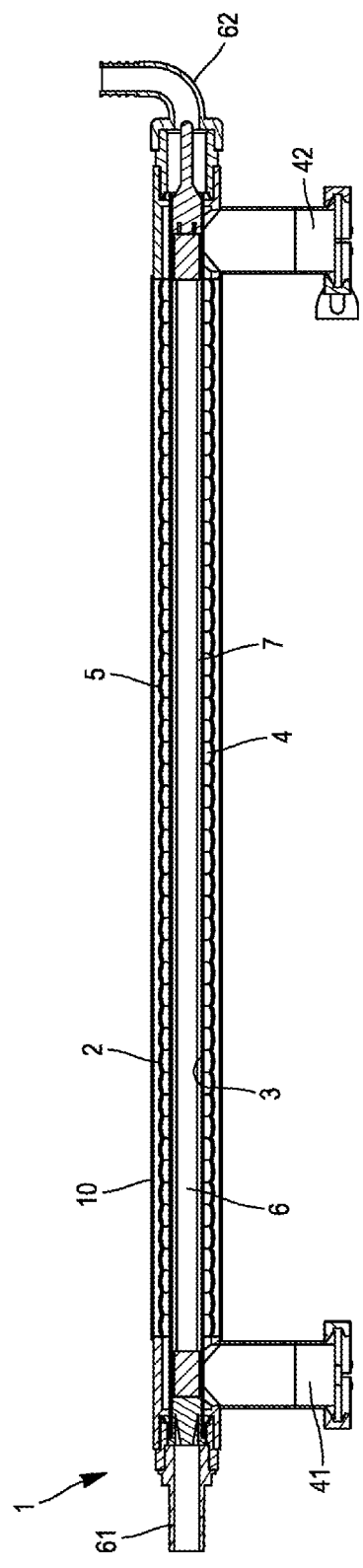

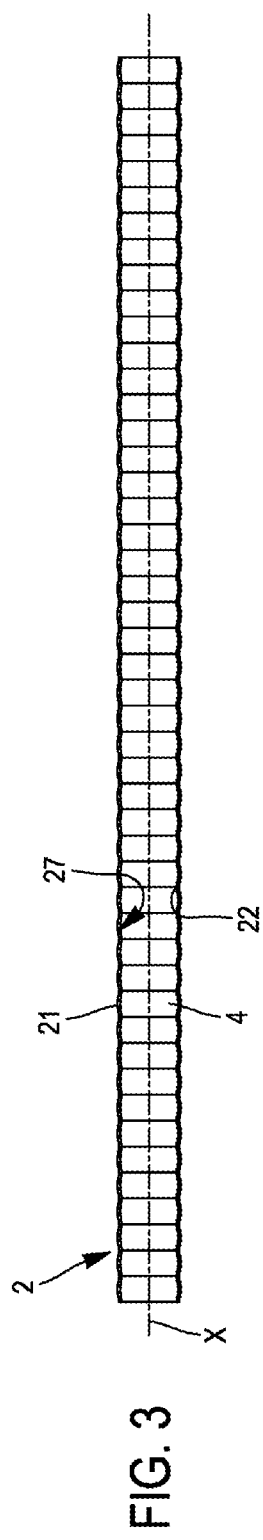
FIG. 3
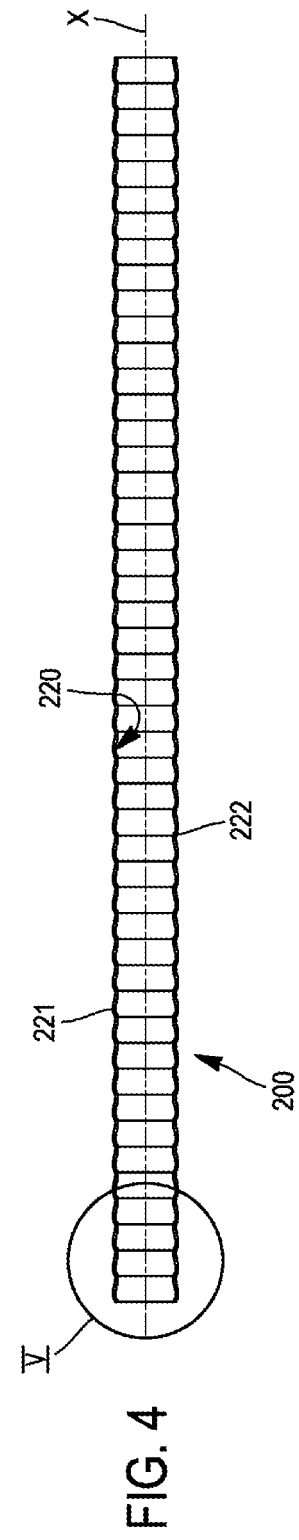
FIG. 4
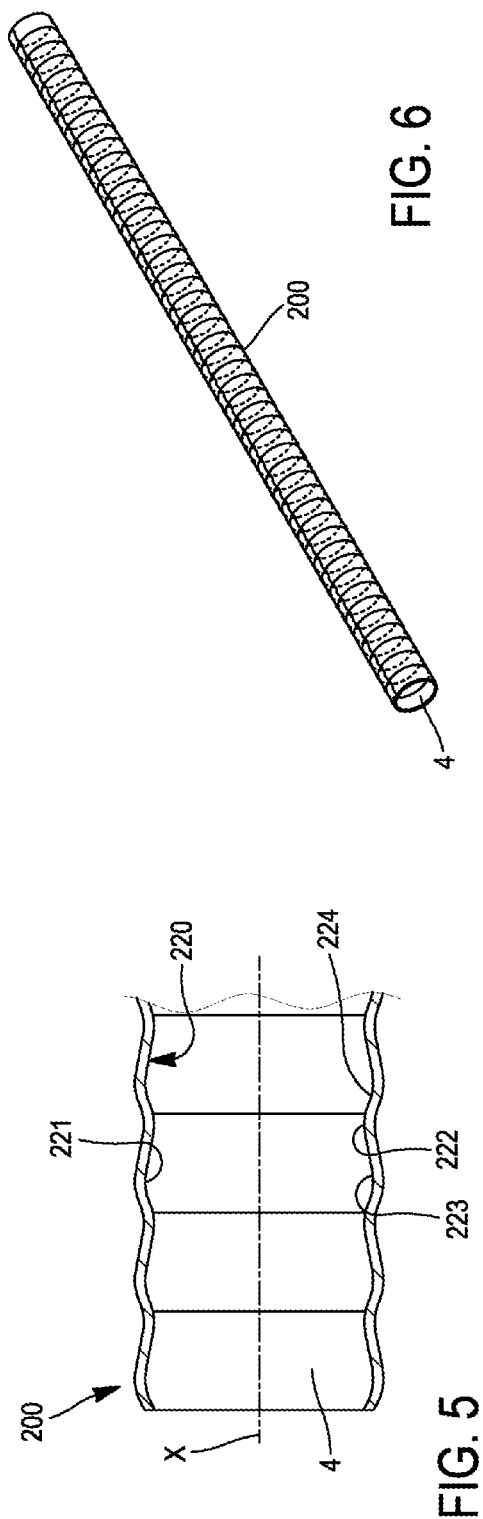
FIG. 5
FIG. 6

DEVICE FOR DECONTAMINATING A TURBID LIQUID

TECHNICAL FIELD OF THE INVENTION

The invention relates to a device for decontaminating a turbid liquid, in particular a food liquid.

PRIOR ART

The devices for decontaminating a liquid perform decontamination by using ultraviolet rays. For that purpose, as illustrated in document EP1255444, decontamination devices of this kind comprise a sheath comprising at least one external wall and one internal wall so as to delimit a flow space for the liquid that is to be decontaminated. In an internal space radially delimited by the internal wall of the sheath, a source of ultraviolet rays is placed so as to irradiate, through the internal wall of the sheath, the liquid that is to be decontaminated. In order to allow the longest possible exposure, the external wall of the sheath has a surface facing the flow space which is spiral: thus, the movement of the turbid liquid that is to be decontaminated takes place in a helix around the source of ultraviolet rays and no longer parallel to the axis of the sheath. However, it is known that ultraviolet rays cannot penetrate far into turbid liquids. For that reason, to ensure good decontamination of the turbid liquid, it is necessary to have a flow of said liquid which is turbulent. This implies, in the case of the devices described in the prior art, high displacement speeds and therefore high pressures, requiring substantial industrial installations.

DESCRIPTION OF THE INVENTION

The invention has the object of providing a decontamination device which allows optimum decontamination of turbid liquid without this requiring high displacement speeds to obtain the necessary turbulent flow.

To that end, the invention provides for a device for decontaminating a turbid liquid, in particular of food type, comprising a sheath extending longitudinally along an axis X, comprising an external wall and an internal wall which are substantially coaxial with one another and delimiting an annular circulation space for the liquid that is to be decontaminated, a source of ultraviolet rays positioned in a central space delimited by the internal wall of the sheath, coaxially with the annular circulation space, the external wall comprising a cylindrical surface facing the annular circulation space having a profile along a generatrix of the cylindrical surface comprising an alternating succession of concave and convex shapes.

Thus, the fact of having a cylindrical surface facing the annular circulation space having a profile along a generatrix of the cylindrical surface comprising an alternating succession of concave and convex shapes makes it possible to obtain simply and easily a turbulent flow within the annular circulation space with low flow velocities and therefore lower pressures, which makes it possible to reduce the industrial installation of devices for decontaminating a turbid liquid thus equipped.

Advantageously, but optionally, the device for decontaminating a turbid liquid according to the invention has at least one of the following technical features:

- the profile comprises circular arcs;
- the profile comprises at least one segment comprising a succession of alternately concave and convex circular arcs;
- the profile comprises at least one segment of sinusoidal shape;
- the profile comprises at least one wave-shaped segment;
- the cylindrical surface is at least partly hooped in shape;
- the external wall is made of stainless steel;
- the internal wall is made of a material that allows ultraviolet rays to pass through, in particular made of quartz; and
- the source of ultraviolet rays comprises light-emitting diodes.

BRIEF DESCRIPTION OF THE FIGURES

Other features and advantages of the invention will emerge on reading the following description of an embodiment of the invention. In the appended drawings:

FIG. 1 is a front view of a decontamination device according to the invention;

FIG. 2 is a top view in section along II-II of the device of FIG. 1;

FIG. 3 is a front view of a first embodiment of an external wall of the sheath of the decontamination device according to the invention;

FIG. 4 is a front view of a second embodiment of an external wall of the sheath of the decontamination device according to the invention;

FIG. 5 is a view of detail V in section of the external wall of FIG. 4; and

FIG. 6 is a three-dimensional view of the external wall of FIG. 4.

For greater clarity, identical or similar elements are identified with identical reference signs across all the figures.

DETAILED DESCRIPTION OF AN EMBODIMENT

With reference to FIGS. 1 and 2, there follows a description of a device for decontaminating a turbid liquid 1 according to the invention.

The device for decontaminating a turbid liquid 1 according to the invention comprises a casing 10 of generally cylindrical elongate shape having an axis, a longitudinal axis X. The casing 10 surrounds a sheath 5, as well as a source of ultraviolet rays 6 extending longitudinally along the longitudinal axis X and coaxially with both the casing 10 and the sheath 5. The casing 10 comprises, at each of its ends, means of access and connection 61, 62 to the source of ultraviolet rays 6. For example, the source of ultraviolet rays 6 is a mercury lamp known per se, or else light-emitting diodes. Of course, other systems emitting ultraviolet rays can be used in the device for decontaminating a turbid liquid 1 according to the invention.

The sheath 5 has a generally cylindrical shape having a longitudinal axis X, in particular the general shape of a cylinder of revolution. It comprises an external wall 2 and an internal wall 3 extending opposite and at a distance from each other and coaxial with one another. The two external 2 and internal 3 walls delimit, between them, a circulation space 4 of annular shape in which the liquid that is to be decontaminated is intended to circulate. On the other hand, the internal wall 3 delimits a central space 7, which is radially internal and in which the source of ultraviolet rays 6 is positioned. Thus, the central space 7 is coaxial with and surrounded by the annular circulation space 4 for the liquid that is to be decontaminated.

At each of the ends along the longitudinal axis X of the sheath 5, the annular circulation space 4 for the liquid that is to be decontaminated is fluidically connected respectively to an inlet 41 for the liquid that is to be decontaminated and to an outlet 42 for the liquid that is at that point decontaminated. Here, the inlet 41 and outlet 42 are oriented radially and centrifugally.

The internal wall 3 is made of a material that allows the ultraviolet rays emitted by the source of ultraviolet rays 6 to pass through, so that said ultraviolet rays can diffuse into the annular circulation space 4 during operation of the device for decontaminating a turbid liquid 1 according to the invention. For example, the material used is quartz.

With reference to FIG. 3, there follows a more detailed description of a first embodiment of the external wall 2 for a device for decontaminating a turbid liquid 1 according to the invention. The external wall 2 is made of an inoxidizable material for example, such as 316L food-grade stainless steel. The external wall 2 comprises a cylindrical surface 27 which extends opposite the annular circulation space 4 of the liquid that is to be decontaminated, on one hand, and, on the other hand, opposite and at a distance from the internal wall 3. The cylindrical surface 27 has a bumpy profile along a generatrix of said cylindrical surface 27. The profile along a generatrix of the cylindrical surface 27 comprises an alternating succession of concave shapes 21 and convex shapes 22. It should be noted that the concavity and convexity of the shapes is established in relation to the annular circulation space 4. Illustrated in FIG. 2, the profile along a generatrix of the cylindrical surface 27 comprises concave shapes 21 which are circular arcs and convex shapes 22 which are points protruding into the annular circulation space 4, each one of the projecting points being obtained by the junction of two circular arcs forming the adjacent concave shapes 21. Thus, the cylindrical surface 27 has a hooped shape. In a variant embodiment, the circular arcs are replaced by elliptical arcs.

In a second embodiment of the external wall 200 of the device for decontaminating a turbid liquid 1 according to the invention, illustrated in FIGS. 4 to 6, the external wall 200 comprises, as previously, a cylindrical surface 270 which extends facing the annular circulation space 4 for the liquid that is to be decontaminated, on one hand, and, on the other hand, opposite and at a distance from the internal wall 3. Here too, the cylindrical surface 270 has a bumpy profile along a generatrix of said cylindrical surface 270. Once again, the profile along a generatrix of the cylindrical surface 270 comprises an alternating succession of concave shapes 221 and convex shapes 222. Illustrated in FIGS. 4 and 5, the profile along a generatrix of the cylindrical surface 270 comprises a succession of waves comprising troughs forming the concave shapes 221 and peaks forming the convex shapes 222. Alternatively along the profile, a trough 221 and a peak 222 are connected by a long slope 223 and a short slope 224. As a variant embodiment, the succession of waves forms a sinusoid along the profile along a generatrix of the cylindrical surface 270.

In a further embodiment, the profile along a generatrix of the cylindrical surface 27, 270 comprises a succession of alternately concave 21 and convex circular arcs.

The shape of the profile along a generatrix of the cylindrical surface 27, 270 is chosen depending on the turbid liquid which will be decontaminated by the device for decontaminating a turbid liquid 1 according to the invention. The turbidity and viscosity parameters of the liquid that is to be decontaminated allow a person skilled in the art to choose the shape of the suitable profile so as to optimize the decontamination of the turbid liquid without requiring high displacement speeds to obtain the necessary turbulent flow in the annular space 4 of the device for decontaminating a turbid liquid 1 according to the invention.

Of course, it is possible to make numerous modifications to the invention without departing from the scope thereof.

The invention claimed is:

1. A device for decontaminating a turbid liquid comprising:
    a sheath extending longitudinally along an axis X, comprising an external wall and an internal wall which are substantially coaxial with one another and delimiting an annular circulation space for the liquid that is to be decontaminated,
    a source of ultraviolet rays positioned in a central space delimited by the internal wall of the sheath, coaxially with the annular circulation space, characterized in that the external wall comprises a cylindrical surface facing the annular circulation space having a profile along a generatrix of the cylindrical surface comprising an alternating succession of concave and convex shapes,
    wherein the profile along the generatrix of the cylindrical surface comprises a succession of asymmetrical waves,
    wherein each wave of the succession of waves comprises a hollow forming the concave shape and a peak forming the convex shape,
    wherein a hollow of a first wave in the succession of waves is connected to a hollow of an adjacent wave in the succession of waves by a shorter slope, the peak, and then a longer slope.

2. The device as claimed in claim 1, wherein the profile comprises circular arcs.

3. The device as claimed in claim 1, wherein the profile comprises at least one segment comprising a succession of alternately concave and convex circular arcs.

4. The device as claimed in claim 1, wherein the profile comprises at least one segment of sinusoidal shape.

5. The device as claimed in claim 1, wherein the profile comprises at least one wave-shaped segment.

6. The device as claimed in claim 1, wherein the cylindrical surface is at least partly hooped in shape.

7. The device as claimed in claim 1, wherein the external wall is made of stainless steel.

8. The device as claimed in claim 1, wherein the internal wall is made of a material that allows ultraviolet rays to pass through.

9. The device as claimed in claim 1, wherein the source of ultraviolet rays comprises light-emitting diodes.

10. The device as claimed in claim 8, wherein the internal wall is made of quartz.

11. The device as claimed in claim 1, further comprising an inlet and an outlet for the liquid to be decontaminated, wherein the inlet and outlet are fluidly connected to the annular circulation space.

12. The device as claimed in claim 11, wherein the internal wall is made of a material that allows ultraviolet rays to pass therethrough, the source of ultraviolet rays being positioned in a central space delimited by the inner wall of the sheath, and the inlet and the outlet being oriented radially and centrifugally.

* * * * *